United States Patent
Boyle et al.

(10) Patent No.: US 6,277,149 B1
(45) Date of Patent: Aug. 21, 2001

(54) RAMP-SHAPED INTERVERTEBRAL IMPLANT

(75) Inventors: John W. Boyle, Upper Montclair; Lawrence A. Shimp, Morganville; David R. Kaes, Toms River; John W. Morris, Beachwood; Erik O. Martz, Jackson; Todd M. Boyce, Aberdeen; Mark Daugherty, Allenwood, all of NJ (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

(21) Appl. No.: 09/328,242

(22) Filed: Jun. 8, 1999

(51) Int. Cl.[7] .................................................. A61F 2/44
(52) U.S. Cl. ................................... 623/17.16; 623/17.11; 623/16.11
(58) Field of Search .............................. 623/16.11, 23.51, 623/23.61, 17.11, 17.16; 606/60, 61

(56) References Cited

U.S. PATENT DOCUMENTS

| | | |
|---|---|---|
| 4,349,921 | 9/1982 | Kuntz . |
| 4,714,469 | 12/1987 | Kenna . |
| 4,863,477 | 9/1989 | Monson . |
| 4,932,973 * | 6/1990 | Gendler ........................ 623/23.63 |
| 5,047,058 | 9/1991 | Roberts et al. . |
| 5,306,307 | 4/1994 | Senter et al. . |
| 5,306,309 | 4/1994 | Wagner et al. . |
| 5,314,478 | 5/1994 | Oka et al. . |
| 5,425,772 | 6/1995 | Brantigan . |
| 5,425,773 | 6/1995 | Boyd et al. . |
| 5,443,514 | 8/1995 | Steffee . |
| 5,458,638 | 10/1995 | Kuslich et al. . |
| 5,458,643 | 10/1995 | Oka et al. . |
| 5,489,308 | 2/1996 | Kuslich et al. . |
| 5,514,180 | 5/1996 | Michelson . |
| 5,522,899 | 6/1996 | Heggeness et al. . |
| 5,534,028 | 7/1996 | Bao et al. . |
| 5,534,030 | 7/1996 | Navarro et al. . |
| 5,554,191 | 9/1996 | Lahille et al. . |
| 5,562,738 | 10/1996 | Boyd et al. . |
| 5,571,190 | 11/1996 | Ulrich et al. . |
| 5,591,235 | 1/1997 | Kuslich . |
| 5,607,424 | 3/1997 | Tropiano . |
| 5,645,596 | 7/1997 | Kim et al. . |
| 5,645,598 | 7/1997 | Brosnahan, III . |
| 5,653,761 | 8/1997 | Pisharodi . |
| 5,653,762 | 8/1997 | Pisharodi et al. . |
| 5,658,336 | 8/1997 | Pisharodi . |
| 5,658,337 | 8/1997 | Kohrs et al. . |
| 5,669,909 | 9/1997 | Zdeblick et al. . |
| 5,683,463 | 11/1997 | Godefroy et al. . |
| 5,683,464 | 11/1997 | Wagner et al. . |
| 5,716,415 | 2/1998 | Steffee . |
| 5,728,159 | 3/1998 | Stroever et al. . |
| 5,766,251 | 6/1998 | Koshino . |
| 5,766,252 | 6/1998 | Henry et al. . |

(List continued on next page.)

OTHER PUBLICATIONS

Vich, Jose M. Otero, Anterior Cervical Interbody Fusion With Threaded Cylindrical Bone, 1985, J. Neurosurg., vol. 63, pp. 750–753.

Primary Examiner—David J. Isabella
(74) Attorney, Agent, or Firm—Dilworth & Barrese, LLP (57) ABSTRACT

A ramp-shaped intervertebral implant is disclosed. The implant has a body having a first end, a second end, a top surface and a bottom surface. At least one of the top and bottom surfaces is tapered and converges towards the second end of the body. An opening extends through the body and has one end opening onto the top surface of the implant and the other end opening onto the bottom surface of the implant. The implant can be formed from the diaphysis or metaphysis of a long bone, wherein the intramedullary canal of the long bone defines the opening. Alternately, the implant can be made from any biocompatible material having the requisite strength requirement.

19 Claims, 6 Drawing Sheets

U.S. PATENT DOCUMENTS

| | | |
|---|---|---|
| 5,769,897 | 6/1998 | Härle . |
| 5,776,199 | 7/1998 | Michelson . |
| 5,782,919 | 7/1998 | Zdeblick et al. . |
| 5,785,710 | 7/1998 | Michelson . |
| 5,865,845 | 2/1999 | Thalgott . |
| 5,888,227 | 3/1999 | Cottle . |
| 5,895,428 | 4/1999 | Berry . |
| 5,904,719 | 5/1999 | Errico et al. . |

* cited by examiner

RAMP-SHAPED INTERVERTEBRAL IMPLANT

BACKGROUND OF THE INVENTION

1. Technical Field

The present disclosure relates generally to intervertebral implants for spinal fusion and, more particularly, to a ramp-shaped intervertebral implant having a top surface and a bottom surface and at least one opening extending between the top and bottom surfaces.

2. Background of Related Art

Surgical procedures for fusing adjacent vertebrae together to treat back pain in patients with ruptured or degenerated intervertebral discs, spondylolisthesis or other pathologies are well known. Typically during such a procedure, a spinal implant is placed into the intervertebral space in a position to engage adjoining vertebrae. The implant is constructed from a biocompatible material which is adapted to fuse with the adjacent vertebrae to maintain proper spacing and lordosis between the adjacent vertebrae, i.e., maintain the disc space.

A variety of different types of intervertebral implants have been developed to perform this function including spinal fusion cages, threaded bone dowels and stepped bone dowels. Exemplary implants are disclosed in U.S. Patent Applications filed on even date herewith, under Certificate of Express Mail Label Nos. EL260888080US and EL071686220US, and entitled "Intervertebral Implant" and "Keyed Intervertebral Dowel", respectively, the entire disclosures of which are incorporated herein by reference.

One type of intervertebral implant has a wedge configuration. U.S. Pat. No. 5,425,772 to Brantigan discloses a wedge-shaped implant having an anterior end, a posterior end, front and rear walls, top and bottom walls and sidewalls. The implant is constructed from biocompatible carbon reinforced polymer or alternately of traditional orthopedic implant materials such as chrome cobalt, stainless steel or titanium. The top and bottom walls are tapered from the anterior end of the implant to the posterior end such that the anterior end of the implant has a height greater than the height of the posterior end of the implant. The top and bottom of the implant are continuous and unslotted and include a series of transverse teeth or serrations extending thereacross. A slot configured to receive bone graft material extends through the implant between the sidewalls.

During insertion of Brantigan's implant into the intervertebral space, the adjoining vertebrae are tensioned and a portion of disc tissue between the vertebrae is cut and removed to form channels between the vertebrae. The implant is positioned in the channel such that the teeth formed on the top and bottom surfaces of the implant engage the adjoining vertebrae. During a surgical spinal fusion procedure, two of Brantigan's implants are inserted between the adjoining vertebrae to be fused.

U.S. Pat. No. 5,443,514 to Steffee also discloses a wedge-shaped implant having upper and lower toothed surfaces, a pair of parallel side surfaces, a pair of end surfaces and a plurality of openings extending between the side surfaces. The implant is constructed from an injection molded chopped carbon fiber reinforced polymer. The openings facilitate blood flow and bone growth from one side of the implant to the other. Steffee's implant is adapted to receive an insertion tool which during insertion of the implant between adjoining vertebrae rotates the implant from a horizontal to a vertical orientation. During a surgical procedure, two of Steffee's implants are positioned between adjoining vertebrae.

Conventional wedge-shaped intervertebral implants, including those described above, have several drawbacks. For example, although autograft wedges are known, e.g., iliac crest wedges, typically, conventional wedge-shaped implants are constructed from materials which do not remodel but rather remain in place forever or until removal is necessitated, i.e., at least some or all of the implant is not replaced by new bone, but rather the implant itself is incorporated into the body. Since the implants usually become adherent to the adjoining vertebrae, if removal of the implant is ever necessitated, the procedure to effect removal is complicated and dangerous to the patient. Moreover, in conventional wedge-shaped implants, the opening(s) to facilitate bone ingrowth extend transversely through the implant and as such do not open in communication with the adjoining vertebrae. Thus, bone ingrowth and eventual fusion will occur more slowly.

Accordingly, a need exists for an improved wedge-shaped intervertebral implant which can be easily manufactured from a material which will be remodeled within the body and will more quickly become adherent to adjoining vertebrae.

SUMMARY

In accordance with the present disclosure, a ramp-shaped intervertebral implant which is constructed from animal or human cadaveric bone or bone composites, or from any biocompatible material having the requisite strength requirements suitable for implantation, is provided. The ramp-shaped implant includes a body having a first side, a second side and upper and lower surfaces. An opening extends through a central portion of the body between the upper and lower surfaces and a series of ridges are formed over at least a portion of at least one of the upper and lower surfaces. The implant decreases in height from the first end of the implant to the second end of the implant.

In a preferred embodiment, the implant is formed from the diaphysis or metaphysis of a long bone. More particularly, the implant is formed by first cutting a cortical ring from a long bone. Next, the cortical ring is secured within a holding fixture and the sidewalls of the cortical ring are machined to provide the implant with a desired shape. As such, the implant may retain its natural configuration or some or all of the sidewalls can be machined to form the implant to any configuration including rectangular, circular, C-shaped, etc. The intramedullary canal of the cortical ring defines an opening which extends from the top surface to the bottom surface of the implant. The implant is then placed in a second holding fixture and the top surface is machined to provide the appropriate taper and the ridges. These steps can be performed simultaneously using, for example, a three-dimensional computer operated milling machine. Alternately, the steps can be performed consecutively. Next, the implant is repositioned in the holding fixture and the bottom surface of the implant is machined to provide the appropriate taper and the ridges. The side surfaces may also be machined to vary the width of the implant along the longitudinal axis of the implant. A C-shaped implant can be formed by making a cut across the medial lateral plane of the cortical ring to expose the intramedullary canal. Thereafter, a ramp or taper can be provided in the anterior/posterior plane. Because the implant is constructed of bone, after insertion into the body of a patient, the implant will remodel within the body. New bone of a patient will eventually replace some or all of the implant. Thus, if removal of the implant is ever necessitated, the implanted bone and/or the remodeled bone can be easily reamed out. Moreover, since the opening extends between the top and bottom surfaces of the implant, bone growth material which is packed into the opening directly contacts the adjoining vertebrae. Thus, fusion of the implant and adjoining vertebrae will occur more quickly.

Alternately, the ramp-shaped intervertebral implant can be formed from any biocompatible material having the requisite strength requirements via any known process including but not limited to molding and machining.

BRIEF DESCRIPTION OF THE DRAWINGS

Various preferred embodiments are described herein with reference to the drawings wherein.

DETAILED DESCRIPTION OF PREFERRED EMBODIMENTS

Preferred embodiments of the presently disclosed ramp-shaped intervertebral implant will now be described in detail with reference to the drawings, in which like reference numerals designate identical or corresponding elements in each of the several views.

FIGS. 1–4 illustrate one preferred embodiment of the presently disclosed ramp-shaped intervertebral implant shown generally as 10. Ramp-shaped implant 10 includes a body 12 having a first wall 14, a second wall 16, a pair of sidewalls 18 and 20, an upper surface 22 and a lower surface 24. An opening 26 extends through body 12 from the upper surface 22 to the lower surface 24. Opening 26 opens onto upper and lower surfaces 22 and 24 and is dimensioned to receive bone growth material including bone particles and/or a biocompatible osteoinductive or osteoconductive material.

Upper and lower surfaces 22 and 24 of body 12 converge from first wall 14 to second wall 16 and are configured to engage vertebral end plates after implantation. A series of ridges 28 are positioned on at least a portion of upper and lower surfaces 22 and 24. Ridges 28 extend between sidewalls 18 and 20. The apex of each ridge 28 defines a substantially right angle corner. Ridges 28 are configured to engage the adjoining vertebrae and prevent the implant from backing out of a receiving bed formed between the adjoining vertebrae. Alternately, in order to further prevent the implant from backing out of the intervertebral space, ridges 28 may be angled such that the apex of each ridge points towards second wall 16. Moreover, protrusions other than ridges may be formed on the upper and lower surfaces of the implant, e.g., pyramid or semi-spherical protrusions.

Preferably, implant 10 is formed from cadaveric human or animal bone and/or bone composites. Such composites may include those discussed in U.S. Pat. No. 5,899,939 to Boyce et al. and in U.S. patent application Ser. No. 09/256,447 to Boyce et al., the entire disclosures of which are incorporated herein by reference. Alternately, other biocompatible materials can be used to form the implant. For example, surgical stainless steel, titanium, ceramic hydroxyopatite, polymers, carbon fiber, tantalum, etc., can also be used to construct the implant. Moreover, depending on the particular material used to construct the implant, a variety of different manufacturing procedures can be used to form the implant including machining and molding for example.

Referring to FIGS. 5–9, in a preferred embodiment, the implant is formed from the cortical ring of a long bone, such as the fibula, radius, ulna, humerus, tibia or femur, by first making a pair of transverse cuts A and B across the diaphysis or metaphysis of a long bone C to form a cortical ring D. Typically, larger bone including humerus, tibia and femur are used to form implants for thoracic and lumbar spinal fusion procedures, whereas smaller bones including the ulna, radius and fibula are used to form implants for cervical spinal fusion procedures. Next, cortical ring D is secured within a holding fixture (not shown) and the sidewalls of the cortical ring are machined to provide a substantially rectangular implant E. Alternately, the sidewalls of the implant can be left to their natural configuration or the sidewalls can be machined to form an implant having a variety of other configurations, e.g., circular, triangular, etc. Subsequently, implant E is secured in a second holding fixture (not shown) and upper surface 22 is machined using a computer controlled three-dimensional milling machine to form ridges 28 and to angle the upper surface 22 from first end 14 to second end 16, i.e., provide the taper. The angle is chosen to maintain the natural curvature of the spine. Alternately, a manually operated milling tool can be used to taper upper surface 22 and subsequently form ridges 28. Next, implant E is repositioned in the second holding fixture and lower surface 24 is machined to form ridges 26 and to angle lower surface 24 from first end 14 to second end 16. The intramedullary canal of the cortical ring defines opening 26. Alternately, the taper and ridges may be provided on only one of the upper and lower surfaces of the implant.

Typically, for thoracic and lumbar spinal fusion procedures, the implant has a length of from about 20 mm to about 21 mm, a width of from about 15 mm to about 18 mm, a rear end height of from about 9 mm to about 13 mm and a forward end height from about 11 mm to about 15 mm. For cervical spinal fusion procedures the implant has a length of from about 10 mm to about 15 mm, a width of from about 10 mm to about 15 mm, a rear end height of from about 6 mm to about 10 mm and a forward end height from about 8 mm to about 12 mm. Alternately, the dimensions of the implant may be varied to accommodate the particular procedure to be performed.

Preferably, before long bone D is cut, the bone is partially demineralized by placing the long bone in a 0.6NHCL solution. By demineralizing the bone in this fashion, only the walls of the intramedullary canal and the circumferential surfaces of the bone will be demineralized. The strength imparting surfaces of the ramp implant will not be compromised. Moreover, the bone may be treated using a variety of bone healing enhancing technologies. For example, bone growth factors may be infused into the natural porosity of the bone and/or the bone may be infused with acid to further demineralize the internal matrix of the bone. Both these bone treatments may be performed using the pressure flow system disclosed in U.S. Pat. No. 5,846,484 which is incorporated herein by reference.

Figure 1:
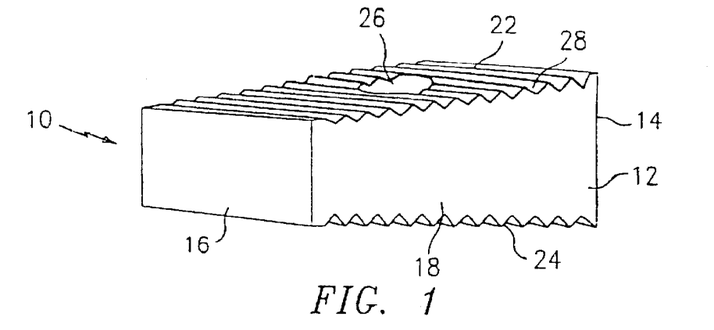
FIG. 1 is a perspective view of one embodiment of the presently disclosed ramp-shaped intervertebral implant.
Figure 2:
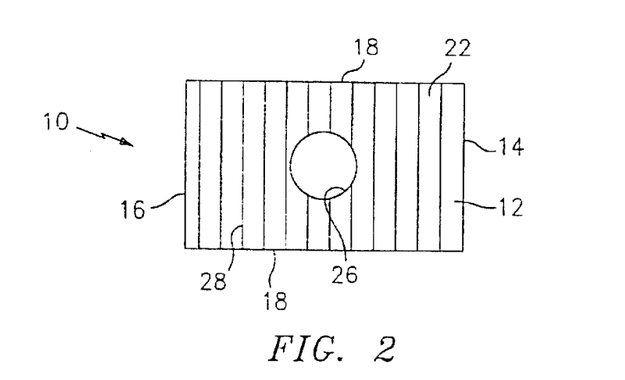
FIG. 2 is a top view of the ramp-shaped intervertebral implant shown in FIG. 1.
Figure 3:
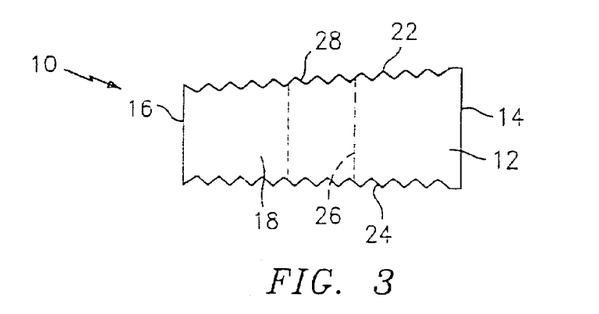
FIG. 3 is a side view of the ramp-shaped intervertebral implant shown in FIG. 1.
Figure 4:
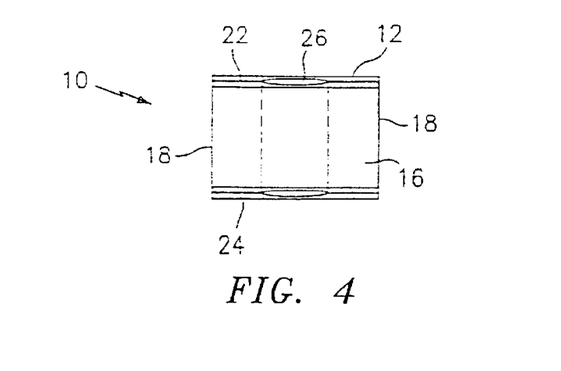
FIG. 4 is a front view of the ramp-shaped intervertebral implant shown in FIG. 1.
Figure 5:
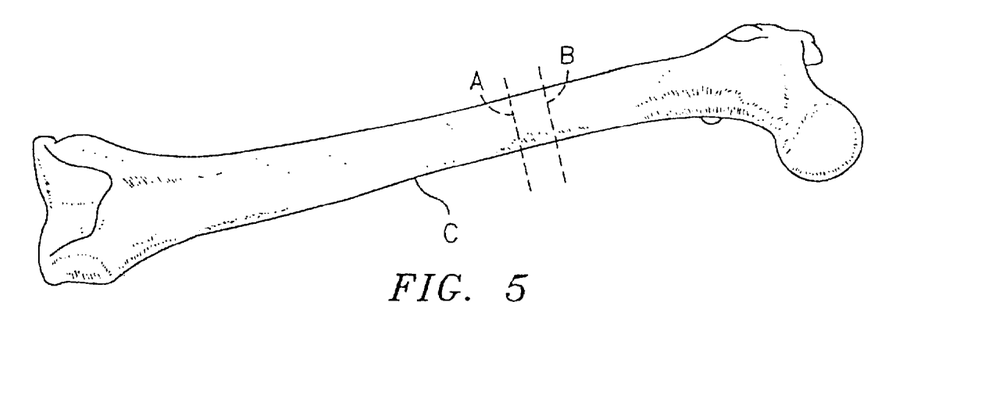
FIG. 5 is a side view of a long bone with cut lines for cutting the cortical ring.
Figure 6:
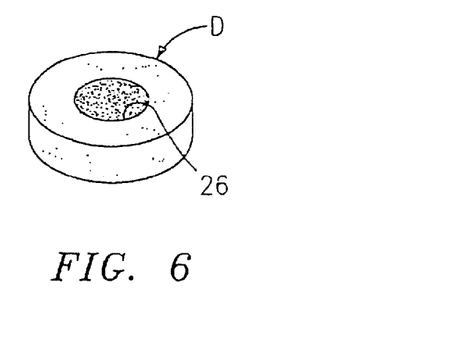
FIG. 6 is a perspective view of a cortical ring cut from the long bone shown in FIG. 5.
Figure 7:
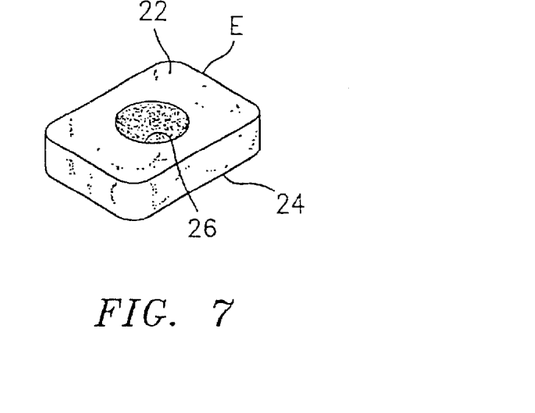
FIG. 7 is a perspective view of the cortical ring shown in FIG. 6 after the sidewalls have been machined.
Figure 8:
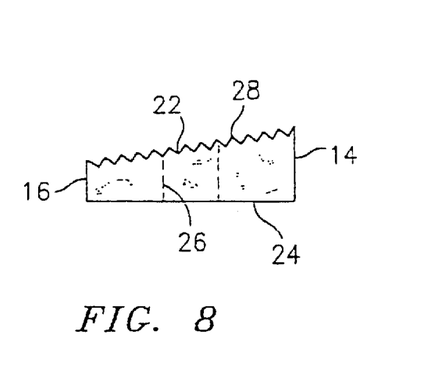
FIG. 8 is a side view of the cortical ring shown in FIG. 6 after the sidewalls and the top surfaces have been machined.
Figure 9:
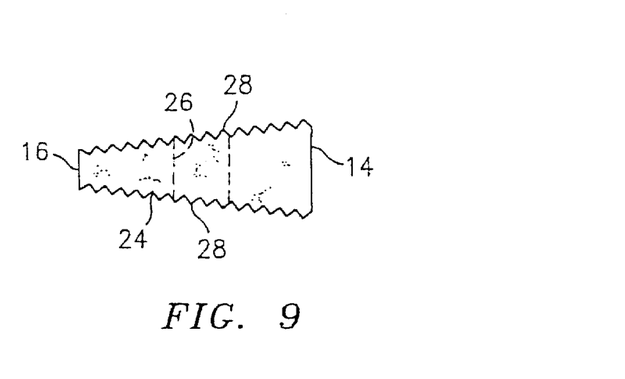
FIG. 9 is a side view of the cortical ring shown in FIG. 6 after the sidewalls, the top surface and the bottom surface have been machined.
Figure 10:
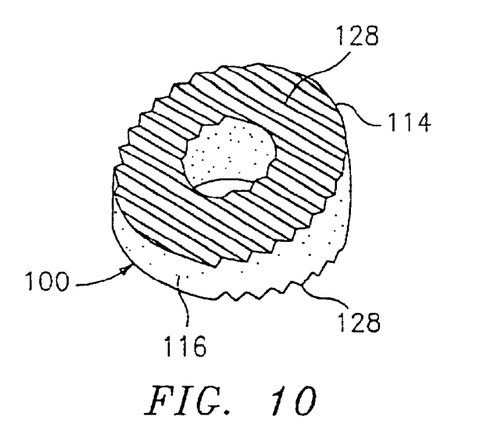
FIG. 10 is a perspective view of another embodiment of the ramp-shaped intervertebral implant.
Figure 11:
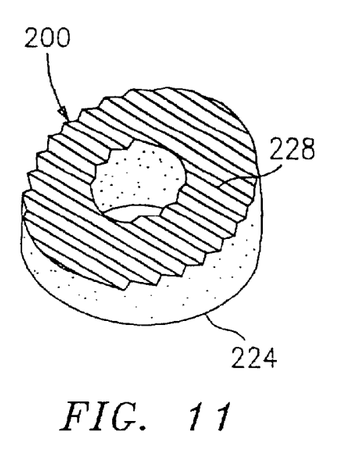
FIG. 11 is a perspective view of yet another embodiment of the ramp-shaped intervertebral implant.
Figure 12:
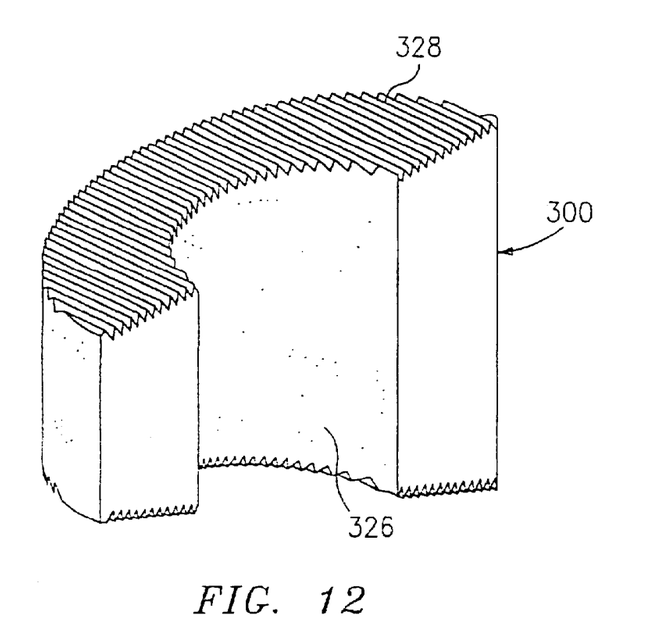
FIG. 12 is a perspective view of yet another embodiment of the ramp-shaped intervertebral implant.

FIGS. 10–12 illustrate alternate embodiments of the ramp-shaped bone intervertebral implant. FIG. 10 illustrates a substantially cylindrical ramp-shaped implant, shown generally as 100. Implant 100 may be formed by machining the sidewall of a cortical ring (FIG. 6) to provide a substantially cylindrical configuration. Alternately, the cortical ring need not be machined but rather, it may retain its natural shape, which depending upon the bone, may vary in shape from cylindrical to triangular in configuration. Implant 110 includes ridges 128 formed on its upper and lower surfaces. The upper and lower surfaces are also machined to taper the implant along its longitudinal axis from the first end 114 of the implant to the second end 116 of the implant.

In an alternate embodiment shown generally as 200 in FIG. 11, the implant is tapered and ridges 228 are formed on only one of the upper and lower surfaces. The other surface 224 remains flat.

In another alternate embodiment shown generally as 300 in FIG. 12, a portion of implant 200 is removed to form a substantially C-shaped ramp implant. C-shaped implant 300 includes an opening 326 and may include protrusions, such as ridges 328, on either or both of the upper and lower surfaces of the implant. C-shaped implant 300 may form any portion of an arc from about 60° C. to 360°.

Figure 13:
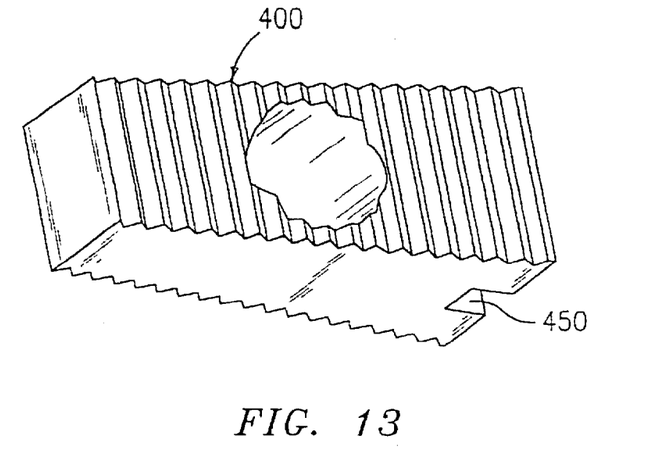
FIG. 13 is a perspective view of yet another embodiment of the ramp-shaped intervertebral implant.
Figure 14:
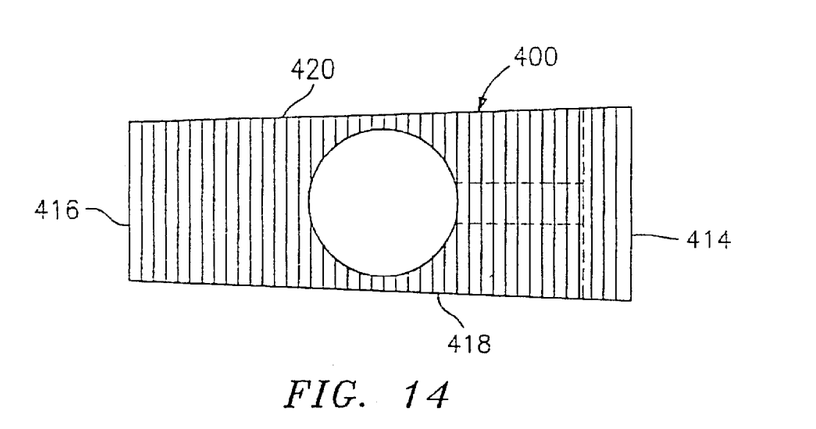
FIG. 14 is a top view of the intervertebral implant shown in FIG. 13.
Figure 15:
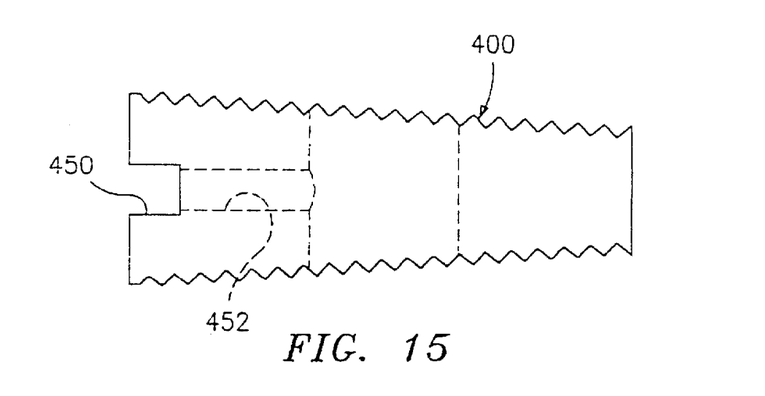
FIG. 15 is a side view of the intervertebral implant shown in FIG. 13.

FIGS. 13–15 illustrate another alternate embodiment of the intervertebral implant shown generally as 400. Intervertebral implant 400 is similar to implant 10 in all respects, except that sidewalls 418 and 420 are also angled to converge toward each other from first wall 414 to second wall 416 along the longitudinal axis of the implant. Implant 400 also includes a slot 450 which communicates with a threaded bore 452. Slot 450 and threaded bore 452 are configured to mate with an implant insertion tool (not shown). Such a slot and threaded bore may be formed on each of the implants discussed above to facilitate insertion of the implant into the intervertebral space.

Figure 16:
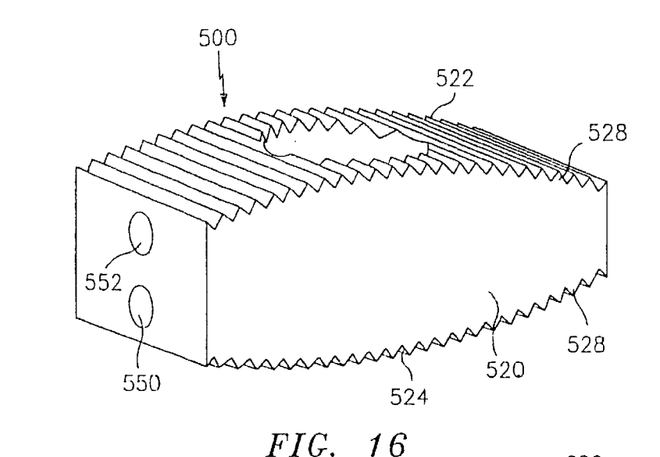
FIG. 16 is a perspective view of another embodiment of the ramp-shaped intervertebral implant.
Figure 17:
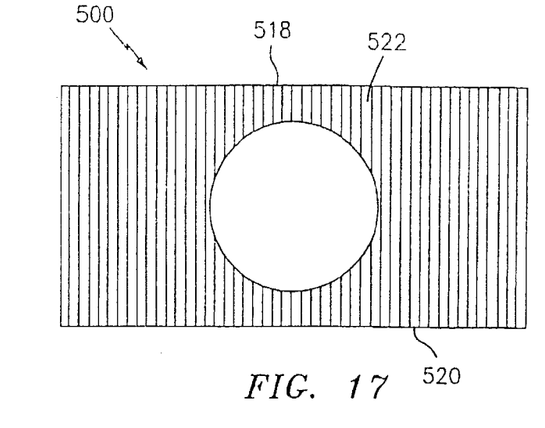
FIG. 17 is a top view of the ramp-shaped intervertebral implant shown in FIG. 16.
Figure 18:
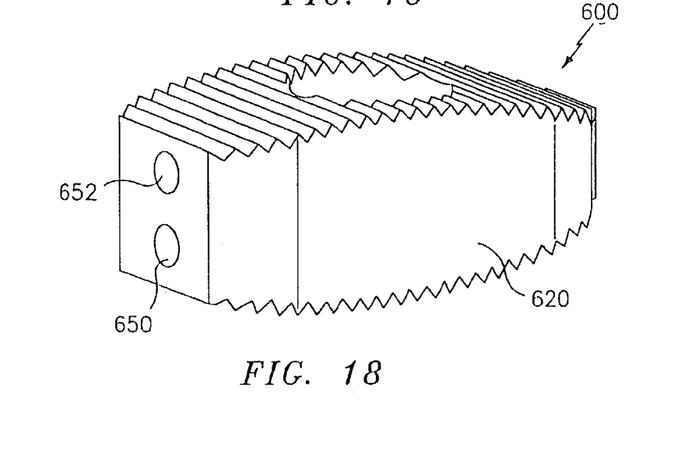
FIG. 18 is a perspective view of another embodiment of the ramp-shaped intervertebral implant.
Figure 19:
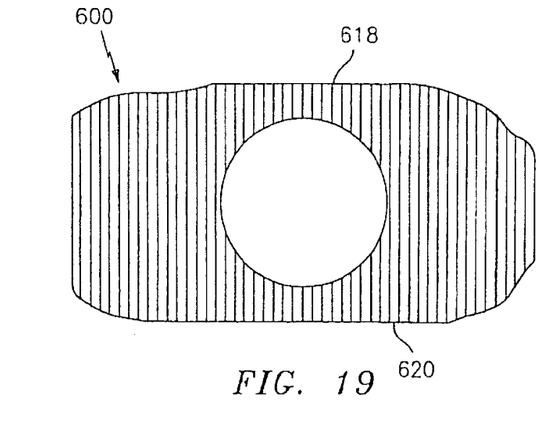
FIG. 19 is a top view of the intervertebral implant shown in FIG. 18.

FIGS. 16–19 illustrate additional alternate embodiments of the ramp-shaped intervertebral implant. FIGS. 16 and 17 illustrate ramp-shaped intervertebral implant 500. Implant 500 is substantially rectangular in shape as viewed from above (FIG. 17). However, the upper and lower surfaces 522 and 524 are convex and include a series of ridges 528. Intervertebral implant 600, illustrated in FIGS. 18 and 19, is substantially identical to implant 500, except that sidewalls 618 and 620 have not been completely flattened as have sidewalls 518 and 520.

Figure 20:
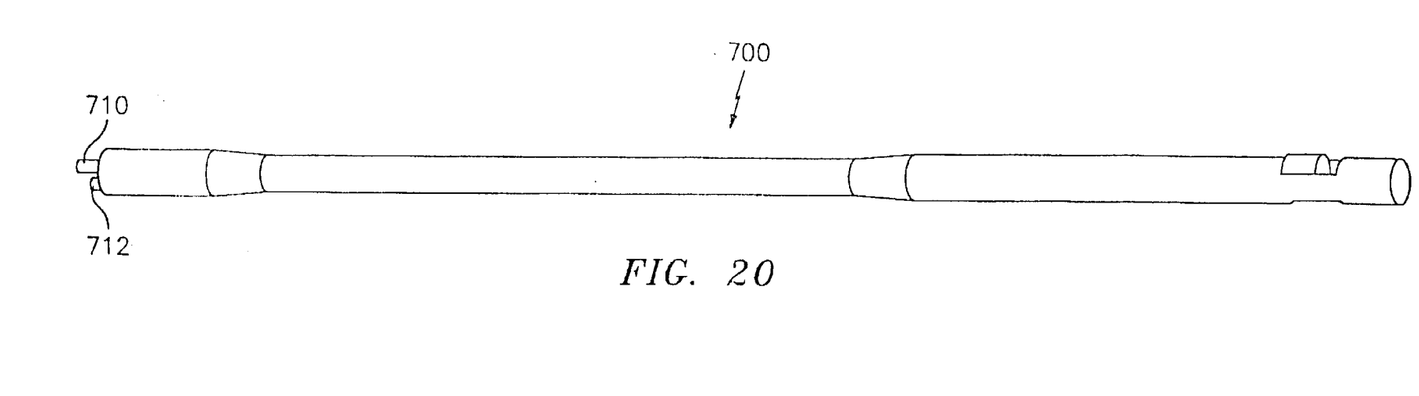
FIG. 20 is a side view of an implant insertion tool.

Both intervertebral implants 500 and 600 include a first wall 514, 614 having a threaded hole 550, 650 and a pilot or threaded hole 552, 652. The holes are configured to engage a threaded prong 710 and a non-threaded prong 712 of an insertion tool 700 (see FIG. 20). Insertion tool 700 facilitates insertion of the implant into the intervertebral space. The spacing of the pilot hole and the threaded hole may be varied on different implants such that only the proper insertion tool can be used to insert an implant into the intervertebral space. This will prevent inadvertent use of the wrong insertion tool with a particular implant. For example, this will prevent the use of instruments designed for inserting implants anteriorly with implants designed to be inserted posteriorly.

Figure 21:
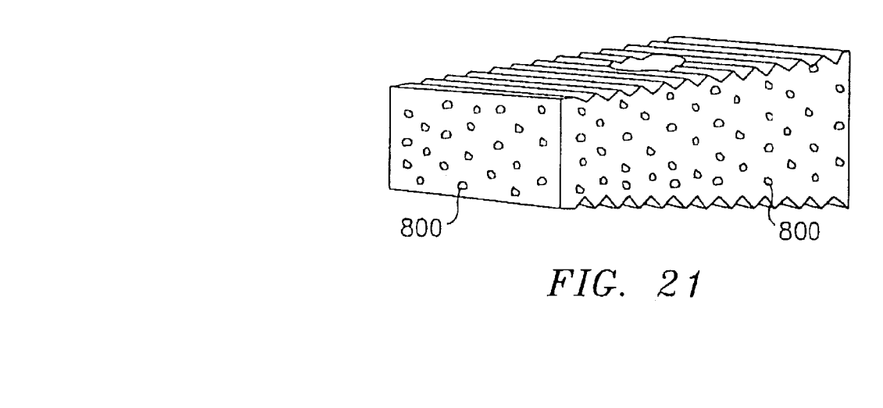
FIG. 21 is a perspective view of another embodiment of the ramp-shaped intervertebral implant.

It will be understood that various modifications may be made to the embodiments disclosed herein. For example, rather than ridges, other protrusions may be formed on the upper and lower surfaces of the implant to retain the implant in a receiving bed formed between adjoining vertebrae. For example, the upper and lower surfaces may be knurled or include dimples or a variety of differently shaped projections. Moreover, any of the implants described above may include perforations 800 along any of its surfaces configured to receive bone growth material. See FIG. 21 for example. Further, the implant can be made using other known methods not disclosed in detail above, including molding and other machining processes. Therefore, the above description should not be construed as limiting, but merely as exemplifications of preferred embodiments. Those skilled in the art will envision other modifications within the scope and spirt of the claims appended hereto.

What is claimed is:

1. A ramp-shaped intervertebral implant comprising:
   a body isolated from along bone having a first end, a second end and top and bottom surfaces, at least one of the top and bottom surfaces being tapered and converging towards the second end of the body, at least one of the top and bottom surfaces having a plurality of protrusions thereon, the protrusions defining substantially V-shaped elongated, parallel grooves, and at least one opening extending through the body having one end opening onto the top surface and one end opening onto the bottom surface, wherein the first end of the implant includes a threaded hole and a non-threaded hole, the holes being dimensioned to engage an insertion tool.

2. A ramp-shaped intervertebral implant according to claim 1, wherein the protrusions include a series of ridges.

3. A ramp-shaped intervertebral implant according to claim 2, wherein the implant includes a pair of substantially parallel side walls, each ridge of the series of ridges having a longitudinal axis that extends in a direction substantially perpendicular to the side walls.

4. A ramp-shaped intervertebral implant according to claim 1, wherein the implant is constructed from the diaphysis or metaphysis of a long bone and the intramedullary canal of the long bone defines the bore.

5. A ramp-shaped intervertebral implant according to claim 1, wherein the implant is formed from bone which is at least partially demineralized.

6. A ramp-shaped intervertebral implant according to claim 1, wherein the implant has a substantially rectangular configuration.

7. A ramp-shaped intervertebral implant according to claim 1, wherein protrusions are formed on both the top and bottom surfaces.

8. A ramp-shaped intervertebral implant according to claim 1, wherein at least one of the top and bottom surfaces is convex.

9. A method for forming a ramp-shaped implant comprising the following steps:

a) making a transverse cut across a long bone having an intramedullary canal to form a cortical ring;

b) machining at least one of top and bottom surfaces of the cortical ring such that the top and bottom surfaces of the cortical ring converge towards one another in a direction towards a second end of the cortical ring, at least one of the top and bottom surfaces having a plurality of substantially V-shaped elongated, parallel grooves, the intramedullary canal of the long bone defining an opening having one end opening onto the top surface of the cortical ring and having a second end opening onto the bottom surface of the cortical ring;

c) machining at least one of the top and bottom surfaces of the cortical ring to form a plurality of protrusions thereon; and;

d) forming a threaded hole and a non-threaded hole in a first end of the implant, the threaded hole and non-threaded hole being dimensional to engage an insertion tool.

10. A method for forming a ramp-shaped implant according to claim 9, wherein the protrusions include a series of ridges.

11. A method for forming a ramp-shaped implant according to claim 10, wherein the machining steps further include use of a three-dimensional milling machine.

12. A method for forming a ramp-shaped implant according to claim 11, wherein steps c) and d) are performed simultaneously using the three-dimensional milling machine.

13. A method for forming a ramp-shaped implant according to claim 9, further including the step of partially demineralizing the bone.

14. A method for forming a ramp-shaped implant according to claim 13, wherein the step of partially demineralizing the bone occurs before the cortical ring is cut from the long bone.

15. A method for forming a ramp-shaped implant according to claim 9, further including the step of:

d) machining sidewalls of the cortical ring to form an implant having a substantially rectangular configuration.

16. A method for forming a ramp-shaped implant according to claim 9, further including the step of:

d) infusing bone growth material into the bone.

17. A method of forming a ramp-shaped implant according to claim 9, further including the step of:

d) forming a plurality of perforations in surfaces of the implant other than the top and bottom surfaces.

18. A method of forming a ramp-shaped implant according to claim 9, wherein at least one of the top and bottom surfaces is convex.

19. A method for forming a ramp-shaped implant comprising the following steps:

a) making a transverse cut across a long bone to form a cortical ring;

b) machining at least one of the top and bottom surfaces of the cortical ring to taper the cortical ring from a first end of the cortical ring to a second end of the cortical ring and to provide a plurality of substantially V-shaped elongated, parallel grooves, the intramedullary canal of the long bone defining an opening having one end opening onto the top surface of the cortical ring and having a second end opening onto the bottom surface of the cortical ring;

c) machining at least one of the top and bottom surfaces of the cortical ring to form a plurality of protrusions thereon; and d) infusing bone growth material into the bone.

* * * * *